(12) United States Patent
Seibel et al.

(10) Patent No.: US 6,461,688 B1
(45) Date of Patent: Oct. 8, 2002

(54) COATING COMPOSITION FOR METAL SUBSTRATES

(75) Inventors: Lawrence P. Seibel, Kenosha, WI (US); Girish G. Parekh, Pittsburgh, PA (US)

(73) Assignee: The Valspar Corporation, Minneapolis, MN (US)

( * ) Notice: Subject to any disclaimer, the term of this patent is extended or adjusted under 35 U.S.C. 154(b) by 0 days.

(21) Appl. No.: 10/117,748

(22) Filed: Apr. 5, 2002

Related U.S. Application Data

(62) Division of application No. 09/302,935, filed on Apr. 30, 1999.

(51) Int. Cl.$^7$ .............................. C08F 2/46; C08F 20/00
(52) U.S. Cl. .................. 427/487; 525/437; 525/445; 525/447; 525/451; 525/539; 525/540; 524/81; 428/458; 428/480; 428/482; 427/207.1; 427/532; 427/557
(58) Field of Search ............................ 525/437, 445, 525/447, 451, 539, 540; 524/81, 458, 480; 428/480, 482; 427/487, 532, 557, 207.1

(56) References Cited

U.S. PATENT DOCUMENTS

| | | | |
|---|---|---|---|
| 4,810,759 A | 3/1989 | Ryntz | |
| 4,873,285 A | 10/1989 | Ryntz | |
| 4,952,626 A | 8/1990 | Kordomenos et al. | |
| 5,393,840 A | 2/1995 | Kuo | |

FOREIGN PATENT DOCUMENTS

| | | |
|---|---|---|
| DE | 1494500 | 12/1969 |
| DE | 38 26 693 | 2/1989 |
| DE | 38 39 905 | 6/1989 |
| EP | 0 086 085 | 6/1986 |
| EP | 0 676 431 | 10/1995 |
| EP | 0 688 840 | 12/1995 |
| GB | 2254328 | 10/1992 |
| JP | 58137659 | 2/1985 |
| JP | 58174113 | 4/1985 |
| JP | 60110291 | 11/1986 |
| JP | 04051074 | 8/1993 |
| JP | 03284733 | 10/1994 |
| WO | WO 96/34924 | 11/1996 |

*Primary Examiner*—Samuel A. Acquah
(74) *Attorney, Agent, or Firm*—Marshall, Gerstein & Borun.

(57) ABSTRACT

A coating composition for application to primed metal substrates as a topcoat is disclosed. The coating composition is especially useful on metal closures for vacuum-packed food products. The coating composition is free of a halide-containing vinyl-polymer and comprises: (a) an acrylate co-polymer having pendant hydroxy groups, (b) a hydroxy-terminated polyester, (c) a crosslinker, and (d) a nonaqueous carrier.

20 Claims, No Drawings

US 6,461,688 B1

COATING COMPOSITION FOR METAL SUBSTRATES

CROSS-REFERENCE TO RELATED APPLICATION

This application is a divisional of U.S. patent application Ser. No. 09/302,935, filed Apr. 30, 1999, now pending.

FIELD OF THE INVENTION

The present invention relates to coating compositions for metal substrates, methods or coaring a metal substrate, and metal articles having a coating composition applied thereon. The coating composition comprises: (a) an acrylate copolymer having pendant hydroxy groups, (b) a hydroxy-terminated polyester, and (c) a crosslinker in (d) a nonaqueous carrier, and is free of a halide-containing vinyl polymer. The coating composition, after curing, is useful as a topcoat for the interior of metal closures and demonstrates excellent flexibility and adhesion to primer coats and to plastisol gaskets.

BACKGROUND OF THE INVENTION

It is well known that an aqueous solution in contact with an untreated metal substrate can result in corrosion of the untreated metal substrate. Therefore, a metal article, such as a metal closure or container for a water-based product, like a food or beverage, is rendered corrosion resistant in order to retard or eliminate interactions between the water-based product and the metal article. Generally, corrosion resistance is imparted to the metal article, or to a metal substrate in general, by passivating the metal substrate or by coating the metal substrate with a corrosion-inhibiting coating.

Investigators continually have sought improved coating compositions that reduce or eliminate corrosion of a metal article and that do not adversely affect an aqueous product packaged in the metal article. For example, investigators have sought to improve the imperviousness of the coating in order to prevent corrosion-causing ions, oxygen molecules, and water molecules from contacting and interacting with a metal substrate. Imperviousness can be improved by providing a thicker, more flexible, and more adhesive coating, but often improving one particular advantageous property is achieved at the expense of another advantageous property.

In addition, practical considerations limit the thickness, adhesive properties, and flexibility of a coating applied to a metal substrate. For example, thick coatings are expensive, require a longer cure time, can be esthetically unpleasing, and can adversely affect the process of stamping and molding the coated metal substrate into a useful metal article. Similarly, the coating should be sufficiently flexible such that the continuity of the coating is not destroyed during stamping and molding of the metal substrate into the desired shape of the metal article.

Investigators also have sought coatings that possess chemical resistance in addition to corrosion inhibition. A useful coating for the interior of a metal closure or container must be able to withstand the solvating properties of the packaged product. If the coating does not possess sufficient chemical resistance, components of the coating can be extracted into the packaged product and adversely affect the product. Even small amounts of extracted coating components can adversely affect sensitive products, such as beer, by imparting an off-taste to the product.

Organic solvent-based coating compositions provide cured coatings having excellent chemical resistance. Such solvent-based compositions include ingredients that are inherently water insoluble, and, thereby, effectively resist the solvating prop-erties of water-based products packaged in the metal container.

Epoxy-based coatings and polyvinyl chloride-based coatings have been used to coat the interior of metal closures and containers for foods and beverages because these coatings exhibit an acceptable combination of adhesion, flexibility, chemical resistance, and corrosion inhibition. Polyvinyl chloride-based coatings and vinyl ace-tate/vinyl chloride copolymer-based (i.e., solution vinyl) coatings also have been the topcoat of choice for the interior of metal closures because these coatings provide excellent adhesion to plastisol sealer gaskets applied over the cured topcoat. However, epoxy-based coatings and polyvinyl chloride-based coatings have serious disadvantages that investigators still are attempting to overcome.

For example, polyvinyl chloride-based coating compositions are thermoplastic. Thermoplastic coatings used as the topcoat of the interior coating of metal closures have inherent performance disadvantages, such as potential softening during the closure manufacturing process or under food processing conditions. Therefore, coating compositions having a thermosetting character have been investigated.

In addition, coatings based on polyvinyl chloride or a related halide-containing vinyl polymer, like polyvinylidene chloride, possesses the above-listed advantageous properties of chemical resistance and corrosion inhibition, and are economical. However, curing a polyvinyl chloride or related lated halide-containing vinyl polymer can generate toxic monomers, such as vinyl chloride, a known carcinogen. In addition, the disposal of a halide-containing vinyl polymer, such as by incineration, also can generate toxic monomers. The generated vinyl chloride thereby poses a potential danger to workers in metal can and closure manufacturing plants, in food process and packaging plants, and at disposal sites. Disposal of polyvinyl chloride and related polymers also can produce carcinogenic dioxins and environmentally harmful hydrochloric acid.

Government regulators are acting to eliminate the use of polyvinyl chloride-based coating compositions that contact food, and thereby eliminate the environmental and health concerns associated with halide-containing vinyl polymers. Presently, however, polyvinyl chloride-based compositions are still used to coat the interior of food and beverage containers and closures.

To overcome the environmental concerns and performance problems associated with polyvinyl chloride-based coating compositions, epoxy-based coating compositions recently have been used to coat the interior of food and beverage containers. However, epoxy-based coatings also possess disadvantages. For example, epoxy-based coating compositions are more expensive than polyvinyl chloride-based coating compositions.

In addition, epoxy-based coatings are prepared from monomers such as bisphenol A and bisphenol A diglycidyl ether (BADGE), for example.

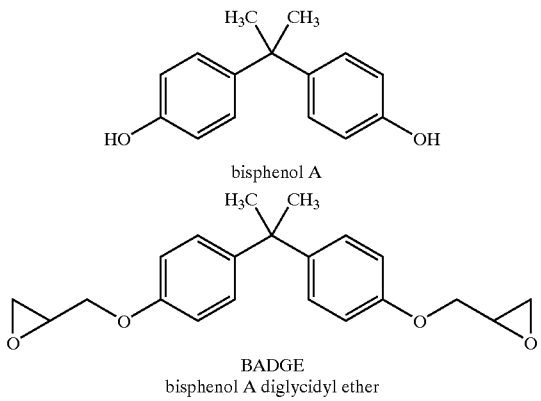

bisphenol A

BADGE
bisphenol A diglycidyl ether

Epoxy resins have a serious disadvantage in that residual amounts of glycidyl ether and bisphenol monomers are present in the resin, typically in an amount of about 0.5% by weight. The presence of such monomers, and especially a glycidyl ether monomer, raises serious environmental and toxicological concerns, especially because a glycidyl ether monomer can be extracted from a cured coating on the interior of a metal container by a product stored in the container. Accordingly, regulatory agencies have promulgated regulations reducing the amount of a glycidyl ether monomer in coating compositions, and especially coating compositions used on the interior of food and beverage containers.

Coating compositions also typically include a phenolic resin. Phenolic resins prepared from bisphenol A or similar bisphenols also can contain residual bisphenol monomers, similar to epoxy-based coatings. Phenolic resins also have disadvantages in that the resins can generate form-aldehyde, which can adversely affect a product stored in a coated metal container. Accordingly, it would be an advance in the art to overcome the problems and disadvantages associated with coating compositions for metal substrates that contain an epoxy resin, a halide-containing vinyl polymer, and/or a phenolic resin.

With respect to a metal closure for a food container, the interior of a metal closure conventionally can be coated with three separate coating compositions, i.e., a three-coat system. First, an epoxy/phenolic primer is applied to the metallic substrate and cured, then a vinyl-based middle coat is applied over the cured primer. Finally, after curing the middle coat, a specially formulated top-coat capable of adhering to a plastisol sealer is applied over the cured middle coat. The plastisol sealer is applied over the cured topcoat, and formed into a gasket during manufacture of a metal closure from a metal sheet having the three cured layers of coatings applied thereon.

Two-coat systems are the primary commercial system, but also exhibit disadvantages. two-coat system for the interior of metal food closure comprises a primer (i.e., a size) and a top-coat. The metal closures typically are used in conjunction with a glass or plastic container. The topcoat must have sufficient adhesion to the primer or the coating will fail. In order to achieve sufficient intercoat adhesion, the chemical make-up of the topcoat often was dictated by the chemical make-up of the primer. Investigators, therefore, are attempting to develop an improved two-coat system for coating the interior of a metal closure, for example, a more "universal" topcoat, i.e., a topcoat that can be applied to a variety of different primers and that exhibits sufficient intercoat adhesion. Such a universal topcoat would be a significant advance in the art.

Two-coat systems have been investigated and used for application to the interior of metal closures. Investigators sought and used topcoat compositions having a sufficiently flexible cured coating such that a coated metal substrate can be deformed without destroying film continuity. This is an important property because the metal substrate is coated prior to deforming, i.e., shaping, the metal substrate into a metal article,. like a metal closure. Coating a metal substrate prior to shaping the metal substrate is the present standard industrial practice.

An ideal two-coat system maintains corrosion inhibition, lowers the cost of applying the coatings, has improved rheological properties, has improved cured film integrity, is free of a polyvinyl chloride-based resin, residual bisphenol monomers, and residual glycidyl ether monomers. In addition, it would be desirable to provide a top coat that acts as a barrier against the migration of bisphenol and glycidyl ether monomers from an epoxy resin-based primer coat.

The coatings used on the interior of a metal food closure also must meet other criteria in addition to performance. For example, the coatings must incorporate components acceptable to the U.S. Food and Drug Administration (FDA) because the cured coating composition contacts food products.

The cured primer and topcoat also require sufficient adhesion to maintain film integrity during closure fabrication. The cured primer and top-coat further require sufficient flexibility to withstand closure fabrication. Sufficient coating adhesion and flexibility also are needed for the closure to withstand processing conditions the closure is subject to during product packaging. Other required performance features of the cured coatings include corrosion protection and adequate adhesion to the plastisol gasket applied over the cured topcoat, sufficient chemical resistance, and sufficient abrasion and mar resistance.

In the manufacture of a metal closure, a metal sheet is coated with the coating compositions, and each coating is cured individually, then the metal sheet is formed into the shape of a metal closure. The closures are made in a variety of sizes ranging from 27 mm (millimeter) to 110 mm in diameter. During manufacture, a plastisol material is applied over the cured coatings on the interior of the metal closure. This plastisol subsequently is formed into a gasket and cured. The gasket ensures an effective seal between the metal closure and glass container, and maintains the vacuum condition of the packaged food product.

Product packaging is performed under processing conditions wherein the plastisol gasket is softened. When the metal closure is pressed onto the glass container, the threads on the glass container form impressions in the softened plastisol gasket. The metal closure is secured in place both by the thread impressions and by the vacuum produced by subsequent cooling. This type of metal closure is used for baby food containers and for other packaged food and beverage products, such as juices and gravies. Other types of closures are designed to be secured to glass containers by lugs rather than by thread impressions in the plastisol.

Vinyl chloride-based topcoat compositions have been softened both by product processing conditions, and by conditions encountered during closure manufacture, thereby leading to closure failure. The present invention is directed, in part, to overcoming such closure failures, and provide an improved two-coat system for the interior of metal closures used for vacuum-packed food products.

Investigators have particularly sought a vinyl halide-free topcoat for the interior of metal closures for food and beverages that retains the advantageous properties of a vinyl chloride-based topcoat, such as adhesion, flexibility, chemical resistance, corrosion inhibition, and favorable economics. Investigators especially have sought a coating composition that demonstrates these advantageous properties and also reduces the environmental and toxicological concerns associated with halide-containing vinyl polymers, formaldehyde, and residual glycidyl ether and bisphenol monomers.

A present topcoat coating composition includes: (a) an acrylate copolymer having pendant hydroxyl groups, typically a hydroxyalkyl (meth-acryl-ate-alkyl (meth)acrylate copolymer, (b) a hydroxy-terminated polyester, and (c) a crosslinker, wherein the composition is free of a halide-containing vinyl polymer, and which, after curing, demonstrates: (1) excellent flexibility, (2) excellent adhesion, to the primer coat, (3) excellent chemical resistance and corrosion inhibition, (4) excellent adhesion to the plastisol gasket, and (5) reduced environmental and toxicological concerns.

As an added advantage, a present topcoat coating composition provides an improved two-coat system, thereby eliminating the presence of a halide-containing vinyl polymer and the presence of residual bisphenol and glycidyl ether monomers, while providing an effective barrier against migration of residual bisphenol and glycidyl ether monomers from the size coat. The present topcoat coating composition also can be used with a variety of types of primers without a significant decrease in coating properties.

SUMMARY OF THE INVENTION

The present invention is directed to a coating composition that, after curing, effectively inhibits corrosion of metal substrates, is flexible, and exhibits excellent adhesion both to a primer coat and to a variety of plastisol gaskets used to ensure the vacuum seal of a metal closure to a glass container. The present coating composition comprises: an acrylate copolymer having pendant hydroxy groups, a hydroxy-terminated polyester, and a crosslinker in a nonaqueous carrier. The present coating composition also is free of (a) a halide-containing vinyl polymer, such as polyvinyl chloride, (b) formaldehyde, and (c) glycidyl ether and bisphenol monomers, such as BADGE and bisphenol A, used in the preparation of an epoxy resin. Never-theless, after curing and crosslinking, the coating compositions demonstrate excellent adhesion both to a primer coat and to a plastisol gasket.

The coating compositions effectively inhibit corrosion of ferrous and nonferrous metal substrates when a composition is applied as a top-coat to a metal substrate, then cured for a sufficient time and at a sufficient temperature to provide a crosslinked coating. A cured and crosslinked coating demonstrates sufficient chemical and physical properties for use as the topcoat of a two-coat system on the interior of metal closures used in packaging foods and beverages. The coating composition does not adversely affect products packaged in a container having a metal closure coated on he interior surface with the cured composition.

In particular, the present coating composition comprises: (a) about 45% to about 90%, by weight of nonvolatile material, of an acrylate copolymer having pendant hydroxy groups, for example, a hydroxyalkyl (meth)acrylate-alkyl (meth) acrylate copolymer, (b) about 10% to about 40%, by weight of nonvolatile material, of a hydroxy-terminated polyester, and (c) about 1% to about 15%, by weight of nonvolatile material, of a crosslinker, wherein the composition is free of a halide-containing vinyl polymer. The weight ratio of hydroxy-containing monomers, e.g., a hydroxyalkyl (meth)acrylate, to alkyl (meth)acrylate in the copolymer is about 1:1 to about 1:50.

Components (a), (b), and (c) are dispersed in a nonaqueous carrier such that the total coating composition includes about 20% to about 80%, by weight of the total composition, of components (a), (b), and (c). Other optional components, such as a curing catalyst, a pigment, a filler, or a lubricant, also can be included in the composition, and, accordingly, increase the weight percent of total nonvolatile material in the composition to above about 80% by weight of the total coating composition.

As used here and hereinafter, the term "coating composition" is defined as the composition including the acrylate copolymer having pendant hydroxy groups, the hydroxy-terminated polyester, the crosslinker, and any optional ingredients dispersed in the nonaqueous carrier. The term "cured coating composition" is defined as the adherent polymeric coating resulting from curing a coating composition. The cured coating composition comprises the acrylate copolymer having pendant hydroxy groups, the hydroxy-terminated polyester, and the crosslinker essentially in the amounts these ingredients are present in the coating composition, expressed as nonvolatile material.

Therefore, one important aspect of the present invention is to provide a coating composition that enhances the ability of the primer to inhibit corrosion of ferrous and nonferrous metal substrates. After application to a primed metal substrate as a topcoat, and subsequent curing at a sufficient temperature for a sufficient time, the coating composition provides an adherent layer of a cured coating composition. The cured coating composition enhances corrosion inhibition, has excellent flexibility, and exhibits excellent adhesion both to a variety of different of primer types applied to the metal substrate and to a variety of different types of plastisol sealer gaskets applied over the cured coating composition.

Because of these properties, an improved two-coat system is available for application to the metal substrate thereby providing economies in time, material, and machinery in the coating of a metal substrate. The coating composition also provides economies because the composition can be used with a variety of primers and plastisol gaskets of different chemical types. The closure manufacturer, therefore, can use the coating composition in a more universal range of applications, which eliminates the need to stock an inventory of different topcoats and eliminates application equipment changeover.

In accordance with another important aspect of the present invention, a cured coating composition demonstrates excellent flexibility and adhesion with respect to the plastisol sealer gasket. The excellent adhesion between the cured coating composition and the plastisol sealer gasket further improves the vacuum seal between a metal closure and a glass container to maintain product integrity, and the excellent flexibility facilitates processing of the coated metal substrate into a coated metal article, like in molding or stamping process steps, such that the cured coating remains in continuous and intimate contact with the primer on the metal substrate.

In accordance with yet another important aspect of the present invention, the cured coating composition demonstrates an excellent flexibility and adhesion even though the coating composition does not include a halide-containing vinyl polymer. Conventional coating compositions include a polyvinyl chloride to impart flexibility to the cured coating and to provide adhesion to the plastisol gasket. However, the presence of polyvinyl chloride adversely affects the heat resistance of the cured composition. A present coating composition, which excludes a halide-containing vinyl polymer (and glycidyl ether and bisphenol monomers), has excellent heat resistance, and, surprisingly, excellent flexibility.

In accordance with yet another important aspect of the present invention, a primed metal substrate coated on at least one surface with a cured coating composition of the present invention can be formed into a metal closure for a glass or plastic container that holds food products. Conventionally, a particular type of topcoat was applied over a particular primer in order to achieve sufficient intercoat adhesion. The present coating composition overcomes this disadvantage, and provides a cured coating composition that exhibits sufficient intercoat adhesion with a variety of types of primers, and with a variety of types of plastisol sealers.

These and other aspects and advantages of the present invention will become apparent from the following detailed description of the preferred embodiments.

DETAILED DESCRIPTION OF THE PREFERRED EMBODIMENTS

A coating composition of the present invention, after curing, provides a cured coating composition that effectively enhances corrosion inhibition of primed metal substrates, such as, but not limited to, aluminum, iron, steel, and copper. A present coating composition, after curing, also demonstrates excellent adhesion to the primer coat applied to the metal substrate and to a plastisol gasket, excellent chemical and scratch resistance, and excellent flexibility.

Accordingly, a coat between the primer and topcoat, i.e., the middle coat, can be eliminated. The present coating compositions, therefore, are useful in an improved two-coat system comprising a primer and a topcoat. The present coating compositions are especially useful as the topcoat of a two-coat system for the interior of a metal closure for vacuum-packed food products, because the topcoat is free of a vinyl halide-containing polymer, residual bisphenol monomers, and residual glycidyl ether monomers, and provides an effective barrier against the migration of residual bisphenol and glycidyl ether monomers from the size coat.

A present coating composition comprises: (a) an acrylate copolymer having pendant hydroxy groups, typically a hydroxyalkyl (meth) acrylate-alkyl (meth)acrylate copolymer, (b) a hydroxy-terminated polyester, (c) a crosslinker, and (d) a nonaqueous carrier. A coating composition of the present-invention is free of a halide-containing vinyl polymer, formaldehyde, and glycidyl ether and bisphenol monomers, like bisphenol A and BADGE. In addition, a present coating composition can include optional ingredients, like a catalyst or pigment, that improve the esthetics of the composition, that facilitate processing of the composition, or that improve a functional property of the composition. The individual composition ingredients are described in more detail below.

(a) Acrylate Copolymer Having Pendant Hydroxy Groups

The coating composition of the present invention comprises an acrylate copolymer having pendant hydroxy groups in an amount of about 45% to about 90%, and preferably about 50 to about 80%, by weight of nonvolatile material. To achieve the Full advantage of the present invention, the coating composition comprises about 55% to about 70%: of the acrylate copolymer, by weight of nonvolatile material.

An acrylate copolymer having pendant hydroxy groups that is useful in the present invention contains about 2 to about 50 weight a, and preferably about 3 to about 40 weight %, of a monomer containing a hydroxy group, for example, hydroxy ethyl meth acrylate. To achieve the full advantage of the present invention, the acrylate copolymer contains about 4 to about 20 weight % of a monomer containing a hydroxy group. Similarly, the alkyl (meth)-acrylate is present in the copolymer in an amount of about 50 to about 98 weight a, preferably about 60 to about 97 weight %, and preferably about 80 to about 96 weight %. The copolymer also can contain 0 to 10 weight %, and preferably 0 to 5 weight %, of an optional mono unsaturated monomer.

The monomer containing a hydroxy group can be any monomer having a carbon-carbon double bond and a hydroxy group. Typically, the monomer is a hydroxyalkyl ester of an α, β-unsaturated acid, or anhydride thereof. The α, β-unsaturated acid can be a monocarboxylic acid or a dicarboxylic acid. Examples of such carboxylic acids include, but are not limited to, acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citraconic acid, mesaconic acid, glutaconic acid, aconitic acid, maleic acid, fumaric acid, tricarboxyethylene, maleic anhydride, and mixtures thereof. As used throughout this specification, the term "(meth)acrylate" is an abbreviation for acrylate and/or meth acrylate.

Specific examples of monomers containing a hydroxy group are the hydroxy ($C_1$–$C_6$) alkyl (meth)-acrylates, e.g., 2-hydroxy ethyl meth acrylate, 2-hydroxy ethyl acrylate, 2-hydroxypropyl methacrvlate, and 3-hydroxypropyl meth acrylate.

The acrylate copolymer also initially can be a copolymer of an α, β-unsaturated acid and an alkyl (meth)acrylate, which then is reacted with a glycol or polyol, e.g., ethylene glycol or propylene glycol, to position pendant hydroxy groups on the acrylate copolymer. The α, β-unsaturated carboxvlic acid can be an acid listed above, for example.

In an alternative embodiment, an acrylate copolymer having pendant glycidyl groups first is formed. The copolymer then is reacted with a reagent to open the glycidyl epoxy ring and position pendant hydroxy groups on the acrylate polymer. The acrylate copolymer having pendant glycidyl groups can be prepared by incorporating a monomer like glycidyl acrylate, glycddyl meth acrylate, allyl glycidyl ether, or vinyl glycidyl ether into the acrylate copolymer.

A preferred monomer containing a hydroxy group is a hydroxyalkyl (meth)acrylate having the following structure:

$$CH_2=\underset{R^1}{C}-\overset{O}{\overset{\|}{C}}=O-R^2-OH,$$

wherein $R^1$ is hydrogen or methyl, and $R^1$ is a $C_1$ to $C_6$ alkylene group or an arylene group. For example, $R^1$ can be, but is not limited to (—$CH_2$—)., wherein n is 1 to 6,

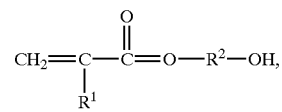

any other structural isomer of an alkylene group containing three to six carbon atoms, or can be a cyclic $C_3$–$C_6$ alkylene group. $R^2$ also can be an arylene group, like phenylene (i.e., $C_6H_4$) or naphthylene (i.e., $C_{10}H_6$) $R^2$ optionally can be sub-stituted with relatively nonreactive substituents, like $C_1$–$C_6$ alkyl, halo, (i.e., Cl, B-, F, and I), phenyl, alkoxy, and aryloxy (i.e., an $OR^2$ substituent).

The monomer containing a hydroxyl group, or the monomer that contains a group (like carboxyl or glycidyl) that can be converted to a hydroxyl group, is copolymerized with an alkyl (meth) acrylate having the structure:

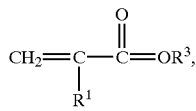

wherein $R^1$ is hydrogen or methyl, and $R^3$ is alkyl group containing one to sixteen carbon atoms.

The $R^3$ group can be substituted with one or more, and typically one to three, moieties such as halo, amino, phenyl, and alkoxy, for example. The alkyl (meth) acrylates used in the copolymer therefore encompass aminoalkyl (meth) acrylates. The alkyl (meth) acrylate typically is an ester of acrylic or methacrylic acid. Preferably, $R^1$ is methyl and $R^2$ is an alkyl group having two to eight carbon atoms. Most preferably, $R^1$ is methyl and $R^2$ is an alkyl group having two to four carbon atoms. Examples of the alkyl (meth) acrylate include, but are not limited to, methyl, ethyl, propyl, isopropyl, butyl, isobutyl, pentyl, isoamyl, hexyl, 2-aminoethyl, 2-ethylhexyl, cyclohexyl, decyl, isodecyl, benzyl, lauryl, isobornyl, octyl, and nonvl (meth) acrylates.

Optional mono unsaturated monomers suitable for copolymerizing with the monomer containing a hydroxy group (or monomer having a group that can be converted to a hydroxy group) and alkyl (meth)-acrylate include, but are not limited to vinyl monomers, like styrene, a halostyrene, isoprene, diallylphthalate, divinylbenzene, conjugated butadiene, a-methylstyrene, vinyl toluene, vinyl naphthalene, and mixtures thereof. Other suitable polymerizable vinyl monomers include acrylonitrile, acrylamide, methacrylamide, methacrylonitrile, vinyl acetate, vinyl propionate, vinyl butyrate, vinyl stearate, isobutoxymethyl acrylamide, and the like.

The hydroxy-containing monomer (or precursor thereof), alkyl (meth) acrylate, and optional mono unsaturated monomers are polymerized by standard free radical polymerization techniques, e.g., using initiators such as peroxides or peroxy esters, to provide a copolymer having a weight average molecular weight ($M_W$) of about 4,000 to about 50,000, and preferably about 6,500 to about 40,000. To achieve the full advantage of the present invention, the copolymer has an $M_W$ of about 7,000 to about 25,000. In the preparation of the copolymer, a chain transfer agent, such as isopropyl alcohol or n-dodecyl mercaptan, can be used to control the $M_W$ of the polymer.

The following example illustrates a hydroxyalkyl (meth) acrylate-alkyl (meth) acrylate copolymer used in the present invention.

EXAMPLE 1

2-Hydroxy ethyl Meth acrylate-Ethyl Meth acrylate Copolymer

Diisobutyl ketone (52.4 lbs.) was added to a clean dry reaction vessel blanketed with nitrogen ($N_2$). The diisobutyl ketone was heated to 230°F., then 0.12 lb. di-t-butylperoxide and 0.12 lb. VAZO 64, an azo polymerization initiator available from Wako Chemicals USA, Dallas, Tex., was added to the heated diisobutyl ketone. Next, 10 wt. % of a monomer premix containing 42.12 lbs. ethyl methacrvlate, 2.20 lbs. hydroxy ethyl meth acrylate, and 0.45 lb. VAZO 64, 0.26 lb. of n-dodecyl mercaptan, and 0.52 lb. di-t-butylperoxide was quickly added to the reactor. The remaining 90 wt.% of the monomer premix then was added to the reactor over a 3-hour time period, while maintaining the temperature of the reaction mixture at 230° F. The vessel holding the monomer mix was rinsed with 0.73 lb. of diisobutyl ketone, which was added to the reactor. After the entire monomer blend and rinse was added to the reactor, the reaction mixture was held at 230° F. for 30 minutes. Then, while maintaining the reaction temperature at 230° F., a solution of 0.68 lbs. t-butyl peroctoate in 0.68 lb. diisobutyl ketone was added to the reaction mixture in twelve equal portions at 15-minute intervals. The resulting reaction mixture was held at 230° F. for 60 minutes, then cooled. The resulting reaction product contained 46% by weight of the ethyl meth acrylate-hydroxy ethyl meth acrylate copolymer. The reaction product weighed about 7.85 lb./gal. The acrylate copolymer contained about 95% ethyl meth acrylate and 5% hydroxy ethyl meth acrylate.

(b) Hydroxy-Terminated Polyester

In addition to the hydroxyalkyl (meth) acrylate-alkyl (meth) acrylate copolymer, a present coating composition also comprises a polyester to impart flexibility to the cured coating composition. The polyester is present in the composition in an amount of about 10% to about 40%, and preferably about 15% to about 35%, by weight of nonvolatile material. To achieve the full advantage of the present invention, the polyester is present in an amount of about 20% to about 30%, by weight of nonvolatile material.

The polyester has a weight average molecular weight ($M_W$) of about 1,000 to about 50,000, and preferably about 2,000 to about 25,000. To achieve the full advantage of the present invention, the polyester has an $M_W$ of about 3,000 to about 20,000.

The identity of the polyester is not especially limited. However, it is important that the polyester is terminated at each end with hydroxy groups. The terminal hydroxy groups of the polyester, along with the pendant hydroxy groups of the acrylate copolymer, are available to react with the crosslinker, and thereby provide a crosslinked acrylate coating.

The polyesters are prepared from an aromatic or aliphatic polycarboxylic acid and an aliphatic diol, triol, or polyol. These ingredients are reacted in appropriate relative quantities to provide a polyester having terminal hydroxy acid groups. Hydroxy groups can be positioned at the terminal end of the polyester by utilizing excess diol, triol, or polyol in the reaction. A triol or polyol is used to provide a branched, as opposed to linear, polyester. Accordingly, the hydroxy-terminated polyesters have a hydroxyl number of about 20 to about 200 mg KOH/g, and preferably about 40 to about 150 mg KOH/g. To achieve the full advantage of the present invention, the polyester has a hydroxyl number of 60 to about 100 mg KOH/g. The polyester has an acid number of about 5 to about 20 mg KOH/g.

Examples of diols, triols, and polyols include, but are not limited to, ethylene glycol, propylene glycol,1,3-propanediol, glycerol, diethylene glycol, dipropylene glycol, triethylene glycol, trimethylolpropane, trimethylolethane, tripropylene glycol, neopentyl glycol, pentaerythritol, 1,4-butanediol, trimethylol propane, hexylene glycol, cyclohexanedimethanol, a polyethylene or polypropylene glycol having an $M_W$ of about 500 or less, isopropylidene bis (p-phenylene-oxypropanol-2), and mixtures thereof.

Examples of polycarboxylic acids or anhydrides include, but are not limited to, maleic anhydride, maleic acid, frumaric acid, succinic anhydride, succinic acid, adipic acid, phthalic acid, phthalic anhydride, 5-terz-butyl isophthatic acid, tetrahydrophthalic anhydride, hexahydrophthalic anhydride, endomethylenetetrahydrophthalic anhydride, azelaic acid, sebacic acid, tetrachloro-phthalic anhydride, chlorendic acid, isophthalic acid, trimellitic anhydride, terephthalic acid, a naphthalene dicarboxylic acid, cyclohexane-dicarboxylic acid, glutaric acid, and mixtures thereof. It is also understood that an esterifiable derivative of a polycarboxylic acid, such as a dimethyl ester or anhydride of a polycarboxylic acid, can be used to prepare the polyester.

A typical polyester is illustrated in Example 2. The diol, polycarboxylic acid, and anhydride, in correct proportions, are reacted using standard esterification procedures to provide a polyester having hydroxy groups at the terminal ends of the polyester.

The following example illustrates a hydroxy-terminated polyester used in the present invention.

EXAMPLE 2

Hydroxy-Terminated Polyester

Neopentyl glycol (38.1 lb.), deionized water (2.0 lb.), adipic acid (38.5 lb.), trimellitic anhydride (4.7 lb.), and isophthalic acid (4.1 lb.) were charged into a reaction vessel as the reaction vessel was heated under a nitrogen ($N_2$) blanket. After the reactants were introduced into the reaction vessel, the reaction mixture was heated until the onset of water distillation. Heating was continued to maintain the overhead column temperature at 210–212° F. The refractive index of the distillate was monitored each hour to remain at 1.337 or below. Heating was continued until the reaction mixture reached 430° F. When the acid number reached 10 mg KOH/g, the reaction mixture was cooled to about 220° F., followed by the addition of 22.2 lbs. of butyl carbitol. The temperature of the reaction mixture was cooled to 150° F. with the addition of 2.8 lb. of butyl carbitol and 2 lbs. of deionized water. The resulting hydroxy-terminated polyester solution contained 75% by weight nonvolatile matter, and had a weight/gallon of 7.95 lbs./gal.

Four hydroxy-terminated polyesters were prepared by the method set forth in Example 2. These polyesters had an $M_W$ of 2,500, 2,700, 1,900, and 5,100.

(c) Crosslinker

The coating composition also contains about 1% to about 25%, and preferably about 3% to about 20%, by weight of nonvolatile material, of a crosslinker. To achieve the full advantage of the present invention, the coating composition contains about 5% to about 15%, by weight of nonvolatile material, of a crosslinker.

The crosslinker is a compound having functional groups that react with hydroxy groups of the acrylate copolymer and the polyester. Cross-linkers that can be included in the coating composition include, for example, benzoguanamine and carbodiimide. Phenolic resins are not used as the crosslinker because such resins contain residual phenol monomers and release formaldehyde.

An aminoplast can be used as the crosslinker. An aminoplast generally is a low molecular weight condensation product between formaldehyde and an amine, like urea or melamine, which then is alkylated using an alcohol. An aminoplast has a low weight average molecular weight in the range of about 1,000 to about 8,000, and preferably from about 3,000 to about 5,000.

A preferred crosslinker is CYMEL® 1125, a benzoguanamine resin, available commercially from Cytec Industries, Wayne, N.J.

(d) Nonaqueous Carrier

A present coating composition is a nonaqueous composition, wherein the acrylate copolymer, the hydroxy-terminaLted polyester, and cross-linker are homogeneously dispersed in a nonaqueous carrier. It should be understood that the present coating composition can include a relatively low amount of water, such as up to about 5% by total weight of the composition, without adversely affecting the corrosion-inhibiting coating composition, either prior to or after curing. The water can be added to the composition intentionally, or can be present in the composition inadvertently, such as when water is present in a particular component included in the coating composition.

In general, the nonaqueous carrier has sufficient volatility to evaporate essentially ertirely from the coating composition during the curing process, such as during heating at about 350° F. to about 400° F. for about 8 to about 12 minutes. Suitable nonaqueous carriers are known in the art of coating compositions, and include, for example, but are not limited to, glycol ethers, like ethylene glycol monomethyl ether, ethylene glycol monoethyl ether, ethylene glycol monobutyl ether, and propylene glycol monomethyl ether; ketones, like cyclohexanone, ethyl aryl ketones, methyl aryl ketones, and methyl isoamyl ketone; aromatic hydrocarbons, like toluene, benzene, and xylene; aliphatic hydrocarbons, like mineral spirits, kerosene,and high flash VM&P naphtha; alcohols, like isopropyl alcohol, n-butyl alcohol, and ethyl alcohol; and aprotic solvents, like tetrahydrofuran; chlorinated solvents; esters; glycol ether esters, like propylene glycol monomethyl ether acetate; and mixtures thereof.

The nonaqueous carrier usually is included in the composition in a sufficient amount to provide a composition including about 20% to about 80% of (a), (b), and (c) by total weight of the composition. The amount of nonaqueous carrier included in the composition is limited only by the desired, or necessary, Theological properties of the composition. Usually, a sufficient amount of nonaqueous carrier is included in the coating composition to provide a composition that can be processed easily and that can be applied to a metal substrate easily and uniformly, and that is sufficiently removed from the coating composition during curing within the desired cure time.

Therefore, essentially any nonaqueous carrier is useful in the present coating composition as long as the nonaqueous carrier adequately disperses and/or solubilizes the composition components, is inert with respect to interacting with composition components, does not adversely affect the stability of the coating composition or the ability of the corrosion-inhibition coating to inhibit corrosion of a metal substrate, and evaporates quickly, essentially entirely, and relatively rapidly to provide a cured coating composition that inhibits the corrosion of a metal substrate, demonstrates good adhesion and flexibility, and has good chemical and physical properties.

(e) Other Optional Ingredients

A coating composition of the present invention also can include other optional ingredients that do not adversely affect the coating composition or a cured coating composition resulting therefrom. Such optional ingredients are known in the art, and are included in a coating composition to enhance composition esthetics, to facilitate manufacturing, processing, handling, and application of the composition, and to further improve a particular functional property of a coating composition or a cured coating composition resulting therefrom.

Such optional ingredients include, for example, catalysts, dyes, pigments, toners, extenders, fillers, lubricants, anticorrosion agents, flow control agents, thixotropic agents, dispersing agents, antioxidants, adhesion promoters, light stabilizers, and mixtures thereof. Each optional ingredient is included in a sufficient amount to serve its intended purpose, but not in such an amount to adversely affect a coating composition or a cured coating composition resulting therefrom.

One optional ingredient is a catalyst to increase the rate of cure. The catalyst is present in an amount of 0% to about 1%, and preferably about 0.05% to about 1%, by weight of nonvolatile material. Examples of catalysts, include, but are not limited to, quaternary ammonium compounds, phosphorous compounds, and tin and zinc compounds, like a tetraalkyl ammonium halide, a tetraalkyl or tetraaryl phosphonium iodide or acetate, tin octoate, zinc octoate, triphenylphosphine, and similar catalysts known to persons skilled in the art.

Another useful optional ingredient is a lubricant, like a wax, which facilitates manufacture of metal closures by imparting lubricity to sheets of coated metal substrate. A lubricant is present in the coating composition in an amount of 0% to about 2%, and preferably about 0.1% to about 2%, by weight of nonvolatile material.

Another useful optional ingredient is a pigment, like titanium dioxide or a toning phenolic resin. A pigment, like titanium dioxide, is present in the coating composition in an amount of 0% to about 50%, and preferably about 10% to about 50%, by weight of nonvolatile material. A pigment, like a toning phenolic resin, is present in an amount of 0% to about 20%, and preferably about 1% to about 10%, by weight of nonvolatile material.

In accordance with an important feature of the present invention, the present coating composition is free of a halide-containing vinyl polymer, such as polyvinyl chloride. The phrase "free of a halide-containing vinyl polymer" is defined as 1.5% or less of a halide-containing vinyl polymer, by weight of nonvolatile material, as discussed hereafter.

Conventionally, a polyvinyl chloride was included in the coating composition to improve composition economics and to improve adhesion of a plastisol gasket material to the cured coating composition. However, a halide-containing vinyl polymer adversely affects the heat resistance of the cured coating composition.

The present composition does not include a halide-containing vinyl polymer, yet has sufficient adhesion to a plastisol gasket to avoid failure of a metal closure for food products. In addition, the present composition exhibits an excellent heat resistance.

In accordance with an important feature of the present invention, a halide-containing vinyl polymer is not intentionally added to the coating composition. However, 1.5% or less of halide-con-training vinyl polymer, i.e., up to about 1.5%, by weight of nonvolatile material, may be present in the coating composition as an inadvertent ingredient. For example, various resins are dust-coated with a halide-containing vinyl polymer as an additive. Incorporating a dust-coated resin into a present coating composition could introduce a halide-containing vinyl polymer into the composition in an amount of up to 1.5% by weight of nonvolatile material. This amount of a halide-containing vinyl polymer does not adversely affect the cured coating composition.

A present coating composition also is free of phenolic resins and epoxy resins. Accordingly, the composition is free of formaldehyde, and of monomers used in the manufacture of epoxy resin, e.g., bisphenols, like bisphenol A, and glycidyl ether monomers, like BADGE. The phrase "free of formaldehyde," is defined as less than 0.1%, by weight, of formaldehyde in the composition. A present composition, therefore, avoids the environmental and toxicological problems associated with such compounds.

A coating composition of the present invention is prepared by simply admixing the copolymer, the polyester, the crosslinker, and any optional ingredients, in any desired order, in the D nonaqueous carrier, with sufficient agitation. The resulting mixture is admixed until all the composition ingredients are homogeneously dispersed throughout the nonaqueous carrier. Then, an additional amount of the nonaaueous carrier can be added to the coating composition to adjust the amount of nonvolatile material in the coating composition on a predetermined level.

To demonstrate the usefulness of a coating composition of the present invention, the following examples were prepared, then applied to a metal substrate as a topcoat, and finally cured to provide a coated metal substrate. The coated metal substrates then were tested, comparatively, for use as a closure for a food or beverage container. The cured coatings were tested for an ability to inhibit corrosion of a metal substrate, for adhesion to the metal substrate and to a plastisol gasket, for chemical resistance, for flexibility, and for scratch and mar resistance.

The following Example 3 illustrates one embodiment of a composition of the present invention and its method of manufacture.

EXAMPLE 3

| Ingredient | Weight Amount (lbs.) | % (by weight of the total composition) | % (by weight of nonvolatile material) |
|---|---|---|---|
| Butyl Cellosolve | 146.62 | 17.71% | — |
| Acrylate Copolymer[1] | 494.15 | 59.67% | 61% |
| Polyester[2] | 125.51 | 15.16% | 25% |
| Crosslinker[3] | 61.74 | 7.46% | 14% |

[1] the hydroxy methacrylate-ethyl methacrylate of Example 1, containing about 46% by weight of nonvolatile material;
[2] the polyester of Example 2, containing about 74% by weight of nonvolatile material; and
[3] CYMEL ® 1125, 85% by weight nonvolatile material.

The composition of Example 3 was prepared by adding the acrylic copolymer, the polyester, and the crosslinker to a portion of butyl cellosolve solvent, stirring until homogeneous, then adding he remainder of the solvent. The resulting coating composition contained 45% by weight nonvolatile material and weighed 8.04 lb./gal. The makeup of the 55% by weight of solvents 18.8% butyl cellosolve, 3.9% butyl carbitol, and 32.3% duisobutyl ketone. The composition of Example 3 contained 0.04%, by weight, formaldehyde.

The coating composition of Example 3 was applied as a topcoat to a metal substrate over a primer, then cured for a sufficient time at a sufficient temperature, such as for about 8 to about 12 minutes at about 350° F. to about 400° F., to provide an adherent, crosslinked, cured coating composition on the metal substrate.

A major function or the cured coating composition of Example 3 is to provide a coating layer that: (1) enhances corrosion inhibition of the metal substrate, and (2) provides a coating capable of adhering to the plastisol gasket. The composition of Example 3 provides a barrier against migration of monomers like bisphenol A and BADG, or formaldehyde, or vinyl polymers when applied over conventional epoxy/phenolic primer coatings.

Conventionally, the primer provides sufficient corrosion-inhibiting properties to adequately protect the metal substrate. However, corrosion inhibition occasionally was insufficient when only one topcoat was applied over the cured primer. Therefore, two topcoats often were used (i.e., a three-coat system). Primers also do not have sufficient adhesion to a plastisol gasket to secure the gasket in place during closure manufacture or food processing.

A coating composition of the present invention, after curing, exhibits excellent chemical and physical properties, exhibits sufficient adhesion to the primer coat to obviate the second top-coat for all except the very aggressive foods packaged in a container, and enhances corrosion inhibition provided by the primer. The present composition also provides excellent adhesion to the plaslsol gasket. In addition, the cured coating composition provided by a coating composition of the present invention is sufficiently adhesive to a variety of different types of primer coats and plastisol gaskets, such that the coating composition can be used in a more universal range of applications.

The coating composition of Example 3 also provided a cured coating composition that exhibited excellent flexibility. Flexibility is an important property of a cured coating composition because the metal substrate is coated with a primer and topcoat prior to stamping or otherwise shaping the metal substrate into a desired metal article, such as a metal container or a metal closure for bottles. The plastisol gasket, if present, is applied over the topcoat during the stamping process.

The coated metal substrate undergoes severe deformations during the shaping process, and if a cured coating composition lacks sufficient flexibility, the coating can form cracks, or fractures. Such cracks result in corrosion of the metal substrate because the aqueous contents of the container or bottle have greater access to the metal substrate. In addition, a cured coating composition provided by a composition of the present invention is sufficiently adhered to the primer during processing into a metal article, thereby further enhancing corrosion inhibition.

The above-described advantages make a coating composition of the present invention useful for application on the interior surface of a variety of metal articles, such as for the interior of vacuum-packed metal containers. The present coating composition is especially useful, after curing, as a corrosion-inhibiting coating on a metal closure for glass or plastic containers that hold food products, like baby food, or food products including volatile acids, like relishes, pickles, and hot peppers.

The compositions of the following Examples 4 through 16 were prepared by the general method outlined above in Example 3. The compositions of Examples 4 through 16 then were applied to a metal substrate as a topcoat over a primer, and cured. The resulting coatings were tested for a variety of properties, and compared to a control composition.

The composition of Examples 4–16 were applied to electrolytic tin plate panels in a sufficient amount to provide 15 mg (milligrams) of cured coating composition per 4 sq. in. (square inches) of panel surface. The compositions of Examples 4–16 were applied over a commercial epoxy-phenolic primer coat. After application to the metal panel, the composition of Examples 4–16 were cured for 8 minutes at 370° F. The compositions of Examples 4–16 were compared to a commercial topcoat composition used on the interior of metal closure, i.e., a polyvinyl chloride-based composition, which also contains a phenolic resin and a pigment. The control composition was applied at a rate of 35 mg per 4 sq. in of the panel.

|  | Ex. 4[1] | Ex. 5 | Ex. 6 | Ex. 7 | Ex. 8 | Ex. 9 |
|---|---|---|---|---|---|---|
| Hydroxyethyl methacrylate-ethyl methacrylate copolymer[2] | 81 | 81 | 60 | 50 | 57.5 | 70 |
| Hydroxy-terminated polyester[3] | 14 | 10 | 25 | 25 | 17.5 | 25 |
| Crosslinker[4] | 5 | 9 | 15 | 25 | 25 | 5 |

[1]percent by weight in the composition;
[2]acrylate copolymer of Example 1;
[3]polyester of Example 2; and
[4]CYMEL ® 1125.

|  | Ex. 10 | Ex. 11 | Ex. 12 | Ex. 13 | Ex. 14 | Ex. 15 | Ex. 16 |
|---|---|---|---|---|---|---|---|
| Hydroxyethyl methacrylate-ethyl methacrylate copolymer[2] | 65 | 65 | 69.4 | 81 | 50 | 70 | 73 |
| Hydroxy-terminated polyester[3] | 10 | 10 | 16.8 | 14 | 25 | 25 | 10 |
| Crosslinker[4] | 25 | 25 | 13.8 | 5 | 25 | 5 | 17 |

[1]percent by weight in the composition;
[2]acrylate copolymer of Example 1;
[3]polyester of Example 2; and
[4]CYMEL ® 1125.

After curing the coating compositions, the panels coated with either the compositions of Examples 4–16 or the control composition were fabricated into metal closures. Tests showed that the compositions of Examples 4–16 passed fabrication of the closures, integrity requirements at elevated temperatures, and compound adhesion tests.

Neither the control nor Examples 4–16 exhibited adhesion failure. in addition, none of the examples exhibited blocking failure. The cured coatings also were subjected to methyl ethyl ketone (MEK) rubs. The MEK rub test measures resistance of a cured coating to chemical attack. In the MEK rub test, cheesecloth saturated with MEK is rubbed back and forth against a coated panel using hand pressure. A rub back and forth is designated as one "double rub." In this test, the cured coating is rubbed until the MEK dissolves or otherwise disrupts the cured coating. A cured coating is less susceptible to chemical attack as the number of MEK double rubs increases. The cured coating of Examples 4–16 required about 25 to about 50 double rubs before the topcoat was broken through. In contrast, the cured control composition broke through after only seven double MEK rubs, even through the control composition was applied at greater than twice the amount of Examples 4–8. These results show that a cured coating composition of the present invention has excellent resistance to chemical attack compared to the control composition, and can be used as the coating for the interior surface of a food or beverage container.

Closures having Example 3 and the control composition as the topcoat were subjected to an accelerated corrosion test by contact with a 2% and 5% by weight acetic acid solution for 30 days and 60 days at 100° F. The composition of Example 3, in different tests, was applied at the rate of 10 mg/in.$^2$, 15 mg/4 in$^2$, and 25 mg/4 in$^2$, and cured at 350° F. or 370° F. In all tests, the composition of Example 3 performed equally or better than the control composition.

This accelerated corrosion test was repeated using Example 3 at a rate of 15 and 25 mg/4 in and cured for 8 minutes at 350° F. and 370° F. The results are summarized below:

| Cure Temp. | Film Weight (mg/4 sq. in.) | 30-day Test[1] | 60-day Test |
|---|---|---|---|
| 370 | 15 | 0.3 | 0 |
| 350 | 15 | 0.2 | 3.2 |
| 370 | 25 | 0.5 | 3.2 |
| 350 | 25 | 0.2 | 2.2 |

[1]average number of pits over six replicate tests.

The results show that Example 3 performed very well as a topcoat for a closure.

The composition. of Example 3 was applied to electrolytic tin plate and tin-free steel at a rate of 15 mg/4 sq. in. and cured at 370° F. for 8 minutes. The coated metal then was formed into mm and 63 mm closures. The closures then were subjected to a variety of tests to determine the suitability of the coating composition as a topcoat for a closure. The closures were rated on a subjective scale of 0 (best) to 10 (worst). A closure passes a particular test if the rating is 5 or less. A rating of 2 is equal to a rating for the control composition. In some instances, the tests are rate with respect to degree of failure.

In particular, various products were packaged in a glass container at 180° F. and immediately sealed with a metal closure. The sealed containers were exposed to food processing conditions, like pasteurization for 30 minutes at 180° F. The containers then were cooled and examined for integrity. The containers also were tested for adhesion of the gasket to the coating.

The present coating compositions passed the cross hatch adhesion test, acetic acid tests, sulfur dioxide tests, cystiene hydrochloride tests, and empty container and water-filled adhesion tests.

In another test, the composition of Example 3 was applied at the rate of 10 mg/4 in$^2$ and 25 mg/4 in$^2$ over a conventional epoxy/phenolic size coating. Extraction tests were performed to determine the barrier properties of the composition of Example 3 with respect extraction of bisphenol A and BADGE from the size coat. The extractions were performed for 2 hours at 250° F., 10% and 50% ethanol, followed by 10 days at 120° F. Test results showed only 26 nanogram/in2 and 17 nanogram/in2 extractions for the 10 mg/4 in$^2$ and 25 mg/4 in$^2$ topcoat applications, respectively. The composition of Example 3, therefore, provides an excellent barrier against extraction of bisphenol and BADGE-type monomers from the size coat.

The properties demonstrated by a coating composition of the present invention, and a cured coating composition resulting therefrom, show that a halide-containing vinyl polymer is not necessary to provide adhesion to a primer coat or a plastisol gasket. The present coating also acts as an effective barrier against migration of formaldehyde, glycidyl ether monomers, and bisphenol monomers from the interior size coat of the closure. The present coating composition, therefore, is useful as a topcoat on the interior of metal closures, and especially metal closures for food and beverage containers.

The elimination of the halide-containing vinyl polymer is important with respect to eliminating the environmental and toxicological concerns associated with such polymers. Surprisingly, the halide-containing vinyl polymer has been eliminated, and the present composition maintains the advantageous physical and chemical properties associated with compositions including a halide-containing vinyl polymer. The present compositions also overcome the environmental and toxicological problems associated with prior epoxy-phenolic-based coatings by eliminating formaldehyde, glycidyl ether monomers, and bisphenol monomers from the composition, and by providing an effective barrier against migration of such monomers from the interior size coat.

The present coating composition can be used in conjunction with a variety of types of primers and plastisol gaskets. The present coating composition, therefore, has a more universal range of applications. The present coating compositions, unlike prior compositions, do not require a pigment, like $TiO_2$, to achieve sufficient performance and film integrity. The performance characteristics of the present coating composition is achieved by a novel combination of ingredients, as opposed to halide-containing vinyl polymers and pigments. The cured coating composition also has a high gloss and tooling wear is reduced during manufacture of the metal closure. These and the above-described advantages make a coating composition of the present invention especially useful for application on the interior surface of a metal closure for food and beverage containers. obviously, many modifications and variations of the invention as herein before set forth can be made without departing from the spirit and scope thereof, and, therefore, only such limitations should be imposed as are indicated by the appended claims.

What is claimed is:

1. A method of coating a metal substrate comprising:
    (a) applying a primer coating composition to at least one surface of the metal substrate;
    (b) heating the metal substrate having the primer coating composition applied thereon for a sufficient time and at a sufficient temperature to cure the primer coating composition and provide a primed metal substrate;
    (c) applying a coating composition to the primed metal substrate, said coating composition comprising:
        (i) about 45% to about 90%, by weight of nonvolatile material, of an acrylate copolymer having pendant hydroxy groups;

(ii) about 10% to about 40%, by weight of nonvolatile material, a hydroxy-terminated polyester;
(iii) about 1% to about 25%, by weight of nonvolatile material, of a crosslinker; and
(iv) a nonaqueous carrier; and
(d) heating the primed metal substrate having the coating composition applied thereon for a sufficient time and at a sufficient temperature to remove the nonaqueous carrier from the composition and provide a crosslinked cured coating composition,
wherein the composition is free of a halide-containing vinyl polymer.

2. The method of claim 1 further comprising 0% to about 2% of a lubricant, 0 to about 50% of a pigment, and 0% to about 1% of a catalyst, each by weight of nonvolatile material.

3. The method of claim 1 wherein the primed metal substrate having the coating composition applied thereon is heated for about 8 minutes to about 12 minutes at a temperature of about 350° F. to about 400° F.

4. A metal article having at least one surface thereof coated with a primer and an adherent layer of a cured coating composition, said cured coating composition resulting from curing a coating composition comprising:
(a) about 45% to about 90%, by weight of nonvolatile material, of a an acrylate copolymer having pendant hydroxy groups;
(b) about 10% to about 40%, by weight of nonvolatile material, a hydroxy-terminaated polyester;
(c) about 1% to about 25%, by weight of nonvolatile material, of a crosslinker; and
(d) a nonaqueous carrier.

5. The metal article of claim 4 wherein the composition is free of a halide-containing vinyl polymer.

6. The metal article of claim 4 further comprising 0%.to about 2% of a lubricant, 0% to about 50% of a pigment, and 0% to about 1% of a catalyst, each by weight of nonvolatile material.

7. The method of claim 1 wherein the acrylate copolymer comprises (a) a monomer containing a hydroxy group and (b) an alkyl (meth) acrylate.

8. The method of claim 7 wherein the weight ratio of monomer containing a hydroxy group to alkyl (meth) acrylate in the copolymer is about 1:50 to about 1:1.

9. The method of claim 1 wherein the acrylate copolymer is prepared by copolymerizing a monomer containing a moiety capable of conversion to a hydroxy group and an alkyl (meth) acrylate, followed by conversion of the moiety to a hydroxy group.

10. The method of claim 1 wherein the coating composition further comprises up to about 1% by weight of nonvolatile material, of a curing catalyst.

11. The method of claim 7 wherein the acrylate copolymer comprises about 3% to about 40% of a monomer having a pendant hydroxy group and about 60% to about 97% of an alkyl (meth) acrylate.

12. The method of claim 1 wherein the hydroxy-terminated polyester has a molecular weight of about 1,000 to about 50,000.

13. The method of claim 1 wherein the coating composition comprises about 3% to about 20% by weight of nonvolatile material of a crosslinker.

14. The method of claim 1 wherein the coating composition includes up to about 1.5%, by weight of nonvolatile material, of a halide-containing vinyl polymer.

15. The metal article of claim 4 wherein the coating composition further comprises up to about 1%, by weight of nonvolatile material, of a curing catalyst.

16. The metal article of claim 4 wherein the coating composition further comprises about 3% to about 20% by weight of nonvolatile material of a cross-linker.

17. The metal article of claim 4 wherein the coating composition further comprises up to about 1.5%, by weight of nonvolatile material, of a halide-containing vinyl polymer.

18. The metal article of claim 4 wherein the acrylate copolymer comprises about 3% to about 40% of a monomer having a pendant hydroxy group and about 60% to about 97% of an alkyl (meth) acrylate, and the hydroxy-terminated polyester has a molecular weight of about 1,000 to about 50,000.

19. The method of claim 1 wherein the hydroxy-terminated polyester is prepared from a diol or triol selected from the group consisting of ethylene glycol, propylene glycol, 1,3-propanediol, glycerol, diethylene glycol, dipropylene glycol, triethylene glycol, trimethylolpropane, trimethyl-olethane, tripropylene glycol, neopentyl glycol, pentaerythritol, 1,4-butanediol, trimethylol propane, hexylene glycol, cyclohexanedimethanol, a polyethylene or polypropylene glycol having an $M_W$ of about 500 or less, isopropylidene bis (p-phenylene-oxypropanol-2), and mixtures thereof and a polycarboxylic acid or anhydride selected from the group consisting of maleic anhydride, maleic acid, fumaric acid, succinic anhydride, succinic acid, adipic acid, phthalic acid, phthalic anhydride, 5-tert-butyl isophthalic acid, tetrahydrophthalic anhydride, hexahydrophthalic anhydride, endomethylenetetrahydrophthalic anhydride, azelaic acid, sebacic acid, tetrachlorophthalic anhydride, chlorendic acid, isophthalic acid, trimellitic anhydride, terephthalic acid, a naphthalene dicarboxylic acid, cyclohexanedicarboxylic acid, glutaric acid, and mixtures thereof.

20. The metal article of claim 4 wherein the acryltate polyester comprises:
(a) about 55% to about 70%, by weight of nonvolatile material, of a hydroxyalkyl (meth) acrylatealkyl (meth) acrylate copolymer containing about 4% to about 20% by weight of a hydroxyalkyl (meth)acrylate;
(b) about 20% to bout 30%, by weight of nonvolatile material, of a hydroxy-terminated polyester having a weight average molecular weight of about 13,000 to about 20,000;
(c) about 5% to about 15%, by weight of nonvolatile material, of a benzoguaniamine crosslinker; and
wherein the composition is free of a halide-containing vinyl polymer.

* * * * *

UNITED STATES PATENT AND TRADEMARK OFFICE
CERTIFICATE OF CORRECTION

PATENT NO. : 6,461,688 B1
DATED : October 8, 2002
INVENTOR(S) : Lawrence P. Seibel et al.

It is certified that error appears in the above-identified patent and that said Letters Patent is hereby corrected as shown below:

Column 19,
Line 14, "0 to about 50%" should be -- 0% to about 50% --
Line 36, "0%.to about 2%" should be -- 0% to about 2% --

Column 20,
Line 28, "trimethyl-olethane," should be -- trimethylolethane --
Line 45, "acryltate polyester" should be -- acrylate polyester --
Line 51, "20% to bout 30%" should be -- 20% to about 30% --

Signed and Sealed this

Eleventh Day of March, 2003

JAMES E. ROGAN
*Director of the United States Patent and Trademark Office*